(12) United States Patent
Scheiber-Mojdehkar et al.

(10) Patent No.: US 7,790,675 B2
(45) Date of Patent: Sep. 7, 2010

(54) METHOD FOR INCREASING FRATAXIN EXPRESSION

(75) Inventors: Barbara Scheiber-Mojdehkar, Vienna (AT); Brigitte Nina Sturm, Vienna (AT)

(73) Assignee: Medizinische Universitaet Wien, Vienna (AT)

( * ) Notice: Subject to any disclaimer, the term of this patent is extended or adjusted under 35 U.S.C. 154(b) by 291 days.

(21) Appl. No.: 11/718,870

(22) PCT Filed: Oct. 27, 2005

(86) PCT No.: PCT/EP2005/011510

§ 371 (c)(1),
(2), (4) Date: Jul. 16, 2007

(87) PCT Pub. No.: WO2006/050819

PCT Pub. Date: May 18, 2006

(65) Prior Publication Data

US 2008/0132687 A1    Jun. 5, 2008

(30) Foreign Application Priority Data

Nov. 9, 2004    (AT) .............................. A 1869/2004

(51) Int. Cl.
*A61K 38/00* (2006.01)
*A61K 38/16* (2006.01)
*C07K 14/505* (2006.01)

(52) U.S. Cl. ............................... 514/2; 514/8; 530/380; 930/90

(58) Field of Classification Search ........................ None
See application file for complete search history.

(56) References Cited

U.S. PATENT DOCUMENTS 4,732,889 A * 3/1988 Cynshi et al. ................... 514/8
5,190,861 A * 3/1993 Hayakawa et al. ......... 435/7.94

FOREIGN PATENT DOCUMENTS

| WO | 00/61164 A1 | 10/2000 |
| WO | WO 01/82953 | 11/2001 |
| WO | 02/053580 A2 | 7/2002 |
| WO | WO 02/064085 | 8/2002 |
| WO | 2004-003176 A3 | 1/2004 |
| WO | 2004/004656 A2 | 1/2004 |

OTHER PUBLICATIONS

Boesch et al., 2008, Movement Disorders, vol. 23, Issue 13, pp. 1940-1944.*
Boesch et al., 2007, Annals of Neurology, vol. 62, pp. 521-524.*
Seznec et al: "2003 International Friedreich's Ataxia Research Conference, Feb. 14-16, 2003, Bethesda, MD, USA" Neuromuscular Disorders, vol. 14, 2004, pp. 70-82, XP002370983.
Taketani: "Aquisition, mobilization and utilization of cellular iron and heme: Endless findings and growing evidence of tight regulation" Tohoku Journal of Experimental Medicine, vol. 205, Apr. 2005, pp. 297-318, XP002370895.
Bradley et al: "Clinical, biochemical and molecular genetic correlations in Friedreich's ataxia." Hum Mol Gen 2000;9: 275-282.
Campuzano et al: "Frataxin is reduced in Friedreich ataxia patients and is associated with mitochondrial membranes." Hum Alol Genet 1997;6: 1771-1780.
Cavadini et al: "Assembly and iron-binding properties of human frataxin, the protein deficient in Friedreich ataxia." Hum Mol Genet. 2002;11: 217-27.
MacFeldet al: "Plasminogen Activator Inhibitor 1 Expression Is Regulated By The Inflammatory Mediators Interleukin-1Alpha, Tumor Necrosis Factor-Alpha, Transforming Growth Factor-Beta And Oncostatin M In Human Cardiac Myocytes," J Moll Cell Cardiol2002;34: 1681-91.
Mateo et al: "Expanded GAA repeats and clinical variation in Friedreich's ataxia." Acta Neural Scand 2004;109: 75-78.
Puccio et al: "Mouse models for Friedreich ataxia exhibit cardiomyopathy, sensory nerve defect and Fe—S enzyme deficiency followed by intramitochondrial iron deposits." Nat Genet 2001; 27: 181-186.
Santos et al: "Frataxin deficiency enhances apoptosis in cells differentiating into neuroectoderm." Hum Mol Genet 2001;10: 1935-1944.
Tan et al: "Ftaraxin expression rescues mitochondrial dysfunctions in FRDA cells." Hum Mol Gen 2001; 19: 2099-2107.
Turano et al: "3-Nitropropionic acid increases frataxin expression in human lymphocytes and in transgenic rat PC12 cells." Neurosi Lett 2003;350: 184-186.

* cited by examiner

*Primary Examiner*—Robert Landsman
*Assistant Examiner*—Ian Dang
(74) *Attorney, Agent, or Firm*—Workman Nydegger

(57) ABSTRACT

Use of human erythropoietin or a derivative of erythropoietin having the biological activity of human erythropoietin of increasing the expression of frataxin for the production of a pharmaceutical preparation for the treatment of Friedreich's ataxia or for the treatment or prevention of a disease associated with Friedreich's ataxia.

8 Claims, 4 Drawing Sheets

METHOD FOR INCREASING FRATAXIN EXPRESSION

The present invention is concerned with a pharmaceutical preparation for the treatment of Friedreich's ataxia and for the treatment or prevention of diseases associated therewith.

Friedreich's ataxia (FRDA) is the most common of the inherited ataxias, affecting 1 in 50,000 people. Clinically, FRDA is characterized by multiple symptoms including progressive gait and limb ataxia, dysarthria, diabetes mellitus and hypertrophic cardiomyopathy (1).

Friedreich's ataxia is caused by a GAA-trinucleotide expansion in the frataxin gene located on chromosome locus 9q13, resulting in a reduced expression of frataxin, a small mitochondrial protein (2). Due to the mitochondrial localization of frataxin, the neurological and cardiological degenerations observed in FRDA are thought to be the result of a mitochondrial defect (3). The exact physiological function of frataxin is unknown, but it may be involved in mitochondrial iron homeostasis and/or assembly of iron-sulfur (FeS) proteins and heme synthesis.

Intramitochondrial iron accumulation has been postulated to initiate the production of hydroxyl radicals by Fenton chemistry, leading to inactivation of FeS enzymes, lipid peroxidation and damage to nucleic acids, proteins and finally resulting in cell death.

There is some debate whether mitochondrial iron accumulation within mitochondria is the result or the cause of the oxidative stress which is responsible for mitochondrial damage. Studies with conditional knockout mouse models and FRDA-patient cells indicate that deficiencies in FeS enzymes precede iron accumulation (4). Clinically there is an intramitochondrial iron accumulation in heart, liver, nervous system and spleen of FRDA-patients, as well as a reduction of mitochondrial DNA, the FeS cluster-containing subunits of the mitochondrial electron transport chain (complex I-III) and of the enzyme aconitase (5). The presence of increased levels of soluble transferrin receptor as indicator for cytosolic iron deficiency is controversial but in general FRDA-patients have normal serum iron and ferritin concentrations. Frataxin is implicated to be necessary for normal heme biosynthesis, but there are no reports that FRDA is commonly associated with anemia.

Stimulation of frataxin with exogenous substances was shown with hemin and butyric acid, and with substances generating reactive oxygen species (such as 3-nitroproprionic acid) (6) or those which are cytotoxic like cisplatin.

There is currently no effective treatment of FRDA available especially for neurological deficits. However, the improved understanding of the role of frataxin has led to the consideration of antioxidants such as Idebenone and iron chelators as potential therapeutic agents. A cardioprotective function of Idebenone was shown in a mouse model. These drugs may have a potential to reduce some clinical features of FRDA, but they cannot cure the disease itself. Another approach to treat FRDA would be gene therapy, which will not be readily available within the near future.

It is therefore the object of the present invention to provide a pharmaceutical preparation for the treatment of Friedreich's ataxia and for the treatment or prevention of a disease associated therewith.

The invention is the use of human erythropoietin or a derivative thereof having the biological activity of human erythropoietin of increasing the expression of frataxin for the production of a pharmaceutical preparation for the treatment of Friedreich's ataxia or for the treatment or prevention of a disease associated therewith.

The term "derivative of human erythropoietin" comprises any polypeptide having the amino acid sequence of erythropoietin but differing in the sugar residue of human erythropoietin, and any mutant or variant of erythropoietin having an amino acid sequence differing from the amino acid sequence of human erythropoietin by at least two amino acids as long as it has the biological activity of erythropoietin of increasing the expression of frataxin.

Variants of erythropoietin are described in e.g. US 2004157293 A1. Derivatives of erythropoietin are described in e.g. Science, Vol. 35, pp. 239-242.

The present invention is concerned with the use of a pharmaceutical preparation containing human erythropoietin, recombinant erythropoietin or derivatives of erythropoietin including all polypeptide variants and a suitable carrier, in a dosage of 400-40,000 Units per week for the treatment of Friedreich's ataxia and/or for the treatment and prevention of a disease associated therewith, which show decreased expression of frataxin.

The pharmaceutical preparation can be administered as solution for injection or infusion, or as lyophilized product, e.g. by the intravenous, intramuscular, intracranial or intranasal route (as nose spray). The invention is further directed to a new medical application of a pharmaceutical preparation containing human erythropoietin, recombinant human erythropoietin or derivatives of erythropoietin including all polypeptide variants of erythropoietin, to increase the expression of the protein frataxin.

The present invention is based on the finding that human erythropoietin and the derivatives described above can significantly increase the expression of frataxin in various cell types, e.g. in primary lymphocytes from FRDA patients in a dose-dependent manner. Therefore human erythropoietin or a derivative thereof described above can be used for the production of a pharmaceutical preparation for the treatment of Friedreich's ataxia or for the treatment or prevention of a disease associated therewith.

Erythropoietin (EPO) is an acidic glycoprotein of approximately 34,000 dalton molecular weight occurring in three forms: $\alpha$, $\beta$ and asialo. The $\alpha$ and $\beta$ forms differ slightly in carbohydrate components, but have the same potency, biological activity and molecular weight. The asialo form is an $\alpha$ and $\beta$ form with the terminal carbohydrate (sialic acid) removed. EPO is present in very low concentrations in plasma when the body is in a healthy state wherein tissues receive sufficient oxygenation from the existing number of erythrocytes.

Erythropoietin possesses biological activities in addition to the erythropoietic effects that originally provided its name. Recently recombinant human EPO (rhuEPO) has received considerable attention due to its broad neuroprotective and cardioprotective capabilities by a still poorly understood mechanism.

We used primary human cardiac fibroblasts and myocytes and tested the influence of rhuEPO on frataxin expression. We found a significant increase in frataxin levels especially in cardiac fibroblasts, where a 2.5 fold increase after 48 hours of rhuEPO could be obtained. This result is important because the main cause of premature death in FRDA is cardiomyopathy. Increasing frataxin expression in the heart can protect the heart from the development of a cardiomyopathy and could therefore increase life expectancy. Moreover, since frataxin is postulated to function as a tissue protective protein, increasing frataxin expression could also represent a new target to treat cardiomyopathy in the general population.

Many cell types produce erythropoietin and many cells besides erythroid progenitors express the erythropoietin-receptor, including cells in the brain. The discovery that neuronal cells produce EPO in response to a variety of insults including ischemia/hypoxia, trauma, immune-mediated inflammation, and excessive neuronal excitation further supports the pleiotropic nature of this cytokine. Using mouse embryonic carcinoma P19 cells (neuronal type) we found significant increases in frataxin expression after incubation with 6.6 U/ml and 9.9 U/ml rhuEPO for 24 and 48 hours (see FIGS. 3A and 3B below). Our experiments with P19 neuronal type cells (see FIG. 4 below) also indicate that EPO-derivatives with shorter plasma half-life than rhuEPO, like asialoerythropoietin could be a good non-erythropoietic alternative to rhuEPO. This can be explained by the fact that only short time incubation with rhuEPO already leads to an increase in frataxin expression and that rhuEPO does not have to be present for a long time to stimulate an increase in frataxin. However, a controlled application of erythropoietically active rhuEPO for certain periods eventually accompanied by phlebotomy in the case of increased hematocrit could also be useful to reduce mitochondrial iron accumulation by triggering mitochondrial heme-biosynthesis and erythropoiesis.

This approach to reduce mitochondrial iron load is currently successfully used in other diseases with mitochondrial iron accumulation like myelodysplastic syndrome and sideroblastic anemia. Such a protocol could be useful especially for patients with large iron deposits in the myocardium and in the dentate nucleus because current clinically available iron chelators do not reach mitochondrial iron deposits.

Over the last decade, rhuEPO has proven to be a safe therapeutic agent in hemodialysis patients with minimal adverse effects. To confirm the in vitro effects of rhuEPO on frataxin-expression, we measured frataxin levels in lymphocytes obtained from haemodialysis patients undergoing rhuEPO treatment. We could find a significant increase (up to 3 fold) in frataxin expression in lymphocytes obtained from dialysis patients 48 hours after receiving rhuEPO compared to lymphocytes obtained from the same patients before rhuEPO-administration. The patients suffered from end stage renal disease and received dosages of EPO ranging from 3,000 to 10,000 U.

This observation indicates that EPO therapy increases frataxin expression in patients. Our data show for the first time that additionally to its neuro- and cardioprotective properties EPO increases frataxin expression.

A preferred embodiment of the present invention is characterized in that said human erythropoietin or said derivative thereof is one of the group consisting of recombinant human erythropoietin, erythropoietin α, erythropoietin β, aranesp, asialoerythropoietin and carbamylated erythropoietin.

A further preferred embodiment of the present invention is characterized in that Friedreich's ataxia is diagnosed by means of gene analysis and/or ELISA and/or realtime-PCR and that expression of frataxin is decreased due to GAA-repeat-expansion or mutations on one or on both alleles in the frataxin gene.

Further preferred embodiments are the use of human erythropoietin or a derivative thereof having the biological activity of human erythropoietin of increasing the expression of frataxin for the production of a pharmaceutical preparation for the treatment or prevention of a disease associated with Friedreich's ataxia, in particular a heart disease of a patient showing decreased expression of frataxin, diabetes of a patient showing decreased expression of frataxin, a neurodegenerative disease of a patient showing decreased expression of frataxin, a bone deformation, in particular scoliosis and pes cavus, of a patient showing decreased expression of frataxin, nystagmus of a patient showing decreased expression of frataxin, impaired hearing of a patient showing decreased expression of frataxin, an eye disease, in particular optic atrophy, of a patient showing decreased expression of frataxin, cancer of a patient showing decreased expression of frataxin.

In the following, the effect of EPO on frataxin expression in various cell types is demonstrated.

Reagents And Antibodies

All chemicals were purchased from Sigma (Vienna, Austria) if not cited otherwise. The primary rabbit polyclonal antibody against mature human and mouse frataxin was prepared as described previously (7); the secondary goat-anti-rabbit horse radish peroxidase conjugated antibody was purchased from DakoCytomation (Vienna, Austria). Recombinant human erythropoietin (epoietin beta) was obtained from Roche, Basel, Switzerland.

Cell Cultures

Lymphocytes—Lymphocytes from 7 FRDA patients (GAA repeats in the range from 240 to 800) were collected from fresh blood samples and isolated with Biocoll Separating Solution, density 1.077 g/ml (Biochrom AG, Berlin, Germany) according to the manufacturer's procedure. Finally, cells were diluted to a density of $1 \times 10^6$ cells and cultured in RPMI media supplemented with 10% fetal calf serum, 2 mM L-glutamine and antibiotics and were used for experiments.

Cardiac cells—Primary cultures of human adult cardiac myocytes and human adult cardiac fibroblasts from patients not suffering from FRDA but undergoing heart transplantation were isolated as described by Macfelda et al. (8). The cells were cultivated in M199 medium containing 10% fetal calf serum as well as 100 U/ml penicillin, 100 μg/ml streptomycin, 10 μg/ml transferrin and 10 μg/ml insulin at 37° C. in a humidified atmosphere of 5% $CO_2$.

Neuronal cells—The P19 clone was obtained from the European Cell Culture Collection (ECACC Cat. Nr. 95102707, Salisbury, UK). Cells were cultured in α-modified Eagle's medium (α-MEM) supplemented with 7.5% calf serum (Euroclone, Vienna, Austria) and 2.5% fetal bovine serum (Gibco, Vienna, Austria), 2 mM L-glutamine, 10 ml/l essential amino acids and antibiotics in a 5% $CO_2$ humidified chamber. Cellular differentiation was carried out as described by Santos et al. (9).

Immunoblotting of Frataxin

Expression of frataxin was detected by Western blot. After treatment with rhuEPO for the indicated periods and after extensive washings the cells were lysed with cell culture lysis reagent (Promega, Vienna, Austria) and transferred to a microcentrifuge tube. Fifty micrograms of proteins were separated on 12% SDS (sodium dodecyl sulfate)—polyacrylamide gel electrophoresis under non-reducing conditions using Prosieve 50 Gel solution (BMA, BioWhittaker from Biozym, Vienna, Austria) and Tris/Tricine-electrode buffer (0.1 M Tris, 0.1 M Tricine, 0.1% SDS, pH 8.3) and electroblotted onto nitrocellulose membranes. Primary antibody was directed against mature frataxin (7) and as a secondary antibody a goat-anti rabbit HRP antibody (1:10000) (DAKO) was used.

Statistical Analysis

Statistical analysis was performed with GraphPad Prism software. Differences were examined for statistical significance using the t-test. Significant differences are marked in the figures with * ($p<0.05$), ($p<0.01$) and * ($p<0.001$). Differences with $p<0.05$ were assumed to be significant.

EXAMPLE 1

Effects of rhuEPO On Frataxin Expression In Isolated Lymphocytes From FRDA Patients Freshly isolated lymphocytes obtained from 7 patients with Friedreich's ataxia (GAA repeats ranging from 240-800) were incubated with various concentrations of rhuEPO for 24 hours. Cell lysates (50 µg protein) were separated on 12% SDS-polyacrylamide gel electrophoresis under non-reducing conditions using Tris/Tricine-electrode buffer (0.1 M Tris, 0.1 M Tricine, 0.1% SDS) and electroblotted onto nitrocellulose membranes. Western blot analysis was performed with a polyclonal antibody against human frataxin.

BRIEF DESCRIPTION OF THE FIGURES

FIGS. 1A and 1B show Western blot densitometric analysis of frataxin expression from three independent experiments. Density of the frataxin band of the control (untreated lymphocytes in the absence of rhuEPO from the same patient) was set as 1 a.u. (arbitrary units). Values represent means±SEM of 3 different experiments. Differences were examined for statistical significance using the paired t-test. Significant differences vs. control are marked in the figures with * ($p<0.05$),  ($p<0.01$) and * ($p<0.001$).

From FIG. 1B it can be seen that the increase in frataxin expression correlates with increasing concentration of rhuEPO. FIG. 1A represents a Western blot for frataxin from one FRDA-patient, where the isolated lymphocytes were treated with different concentrations of rhuEPO for 24 hours.

EXAMPLE 2

Effects of rhuEPO On Frataxin Expression In Human Cardiomyocytes And Cardiofibroblasts The heart is one of the most affected organs in FRDA-patients, therefore we investigated the effects of rhuEPO on frataxin expression in primary cultures of human adult cardiac myocytes (HACMs) and cardiofibroblasts, prepared from ventricular tissue obtained from donor hearts from patients undergoing heart transplantation (8).

Figure 1A:
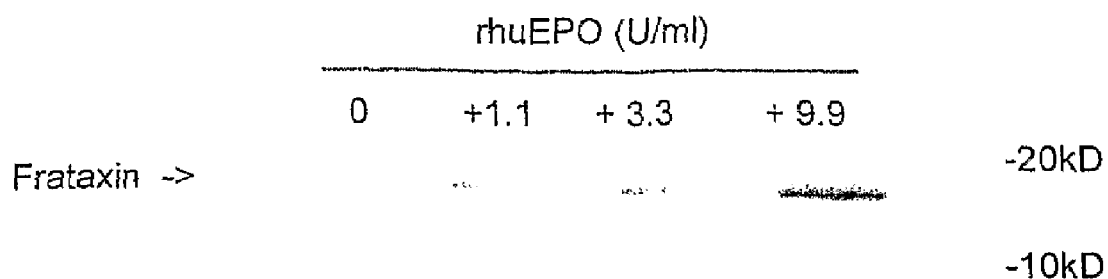
FIG. 1A is an image of a gel showing frataxin expression after administration of rhuEPO.
Figure 1B:
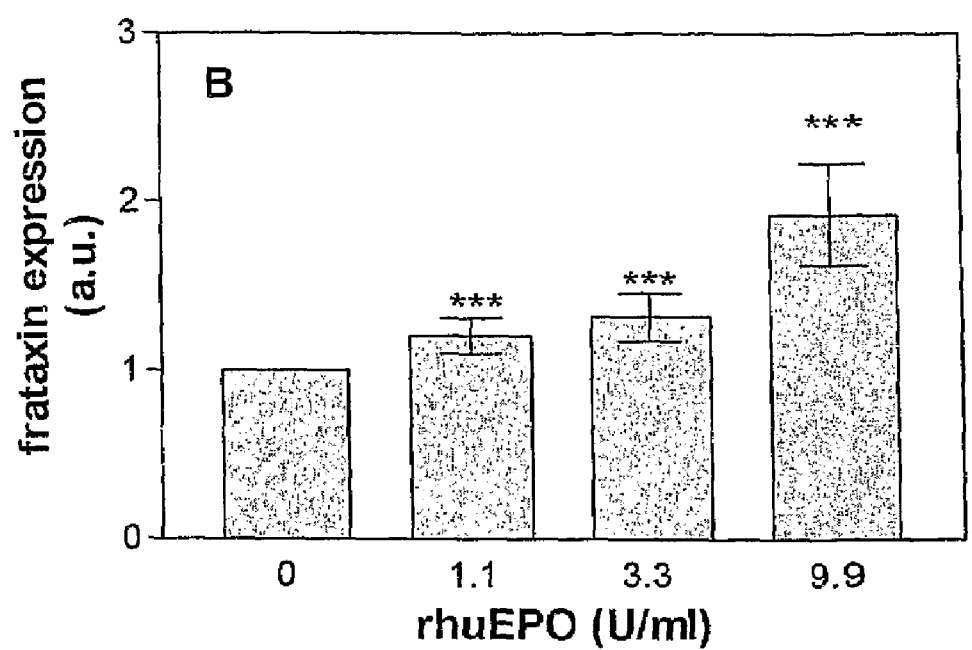
FIG. 1B is a graph showing frataxin expression as a function of rhuEPO.
Figure 2A:
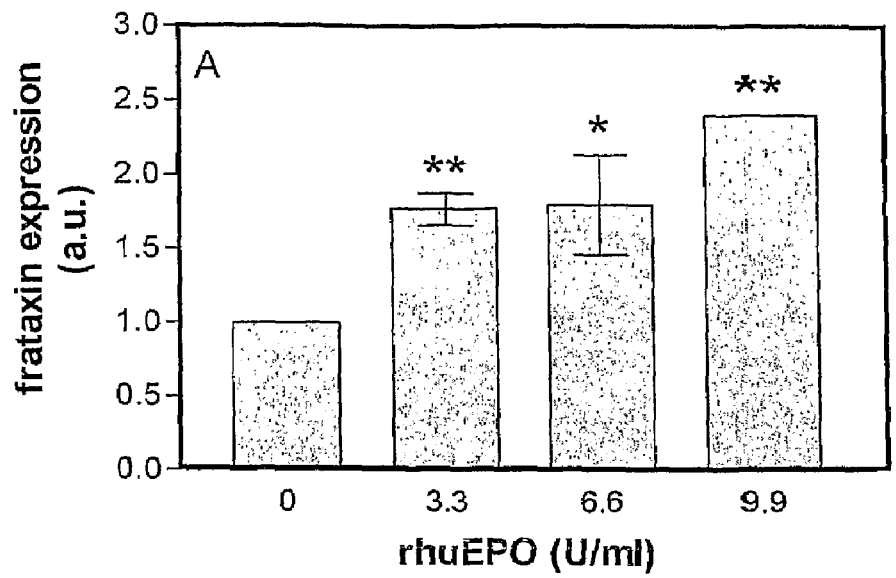
FIG. 2A is a graph showing frataxin expression as a function of rhuEPO.
Figure 2B:
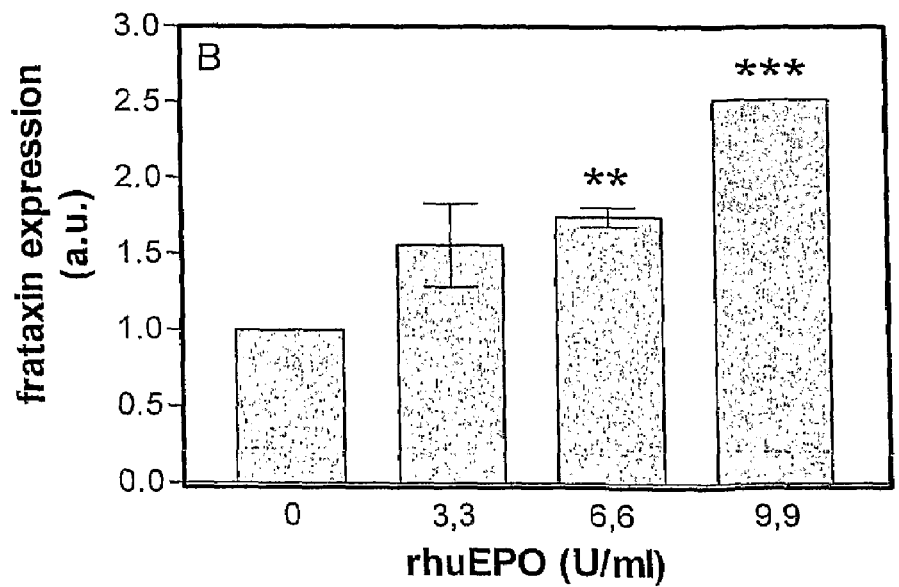
FIG. 2B is a graph showing frataxin expression as a function of rhuEPO.

FIG. 2 shows frataxin-expression in primary human heart cells. Primary cultures of human adult cardiac myocytes (FIG. 2A) and cardiac fibroblasts (FIG. 2B), were incubated with rhuEPO for 48 hours. Cell lysates (40 µg protein) were separated on 12% SDS-polyacrylamide gel electrophoresis under non-reducing conditions using Tris/Tricine-electrode buffer (0.1 M Tris, 0.1 M Tricine, 0.1% SDS) and electroblotted onto nitrocellulose membranes. Western blot analysis was performed with a polyclonal antibody against human frataxin. Densitometric analysis of frataxin expression from three independent experiments is shown. Density of the frataxin band of the control (in the absence of rhuEPO) was set as 1 a.u. (arbitrary units). Values represent means±SEM of 3 different experiments. Some of the error bars are smaller than the symbols. Differences were examined for statistical significance using the paired t-test. Significant differences vs. control are marked in the figures with * ($p<0.05$),  ($p<0.01$) and * ($p<0.001$).

From FIG. 2 A significant increase in frataxin expression in human primary cardiomyocytes (FIG. 2A) and cardiofibroblasts (FIG. 2B) following incubation with rhuEPO can be seen.

EXAMPLE 3

Effects of rhuEPO On Neuronal Frataxin Expression

Mouse embryonic carcinoma P19 cells were differentiated into neuronal cells (9). To investigate the influence of rhuEPO on frataxin expression, the cells were incubated with rhuEPO for 24 h (FIG. 3A) and 48 h (FIG. 3B). Cell lysates (50 µg protein) were separated on 12% SDS-polyacrylamide gel electrophoresis under non-reducing conditions using Tris/Tricine-electrode buffer (0.1 M Tris, 0.1 M Tricine, 0.1% SDS) and electroblotted onto nitrocellulose membranes. Western blot analysis was performed with a polyclonal antibody against human frataxin, which also detects mouse frataxin due to 94% sequence homology. Western blot densitometric analysis of frataxin expression from three experiments is shown. Density of the frataxin band of the control (in the absence of rhuEPO) was set as 1 a.u. (arbitrary units). Values represent means±SEM of 3 different experiments. Differences were examined for statistical significance using the paired t-test. Significant differences vs. control are marked in the figures with * ($p<0.05$) and ** ($p<0.01$).

Figure 3A:
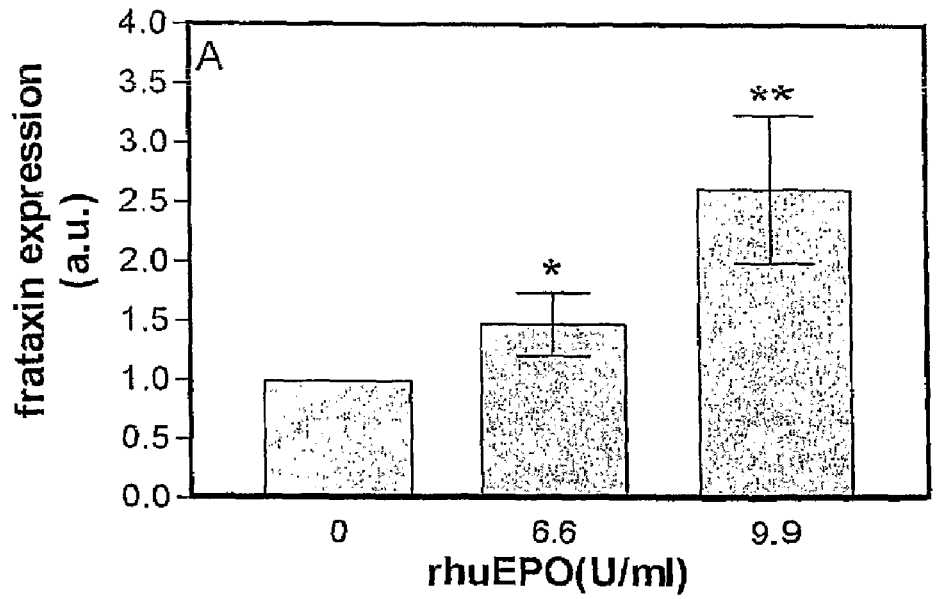
FIG. 3A is a graph showing frataxin expression as a function of rhuEPO.
Figure 3B:
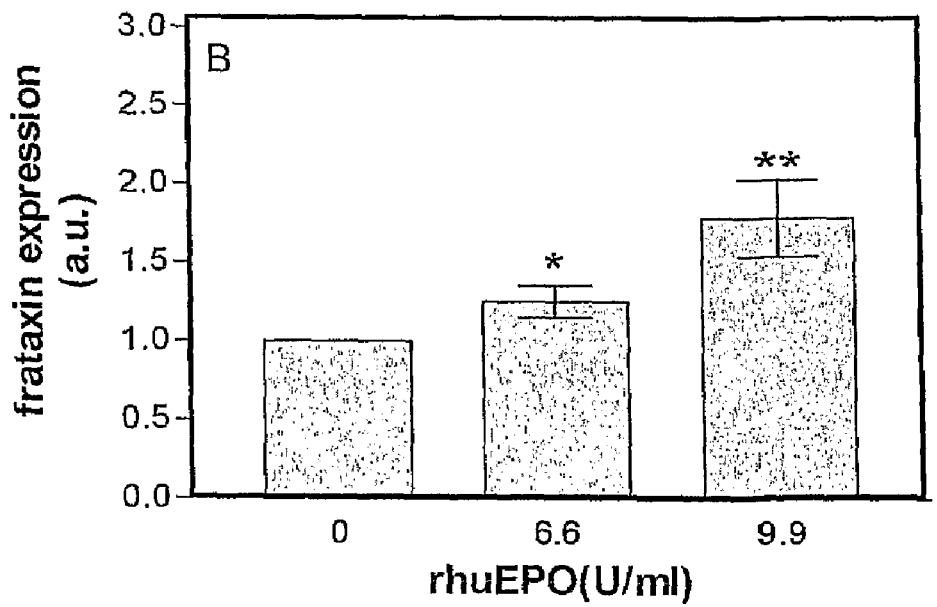
FIG. 3B is a graph showing frataxin expression as a function of rhuEPO.

From FIG. 3 it can be seen that in P19 cells there is a significant increase of frataxin expression following incubation with rhuEPO for 24 hours (FIG. 3A) and 48 hours (FIG. 3B). Frataxin expression increased up to 2.5 fold when the cells were treated with rhuEPO for 24 hours compared to the untreated control cells.

EXAMPLE 4

Effects of Short Time Incubation With rhuEPO On Neuronal Frataxin Expression

This example shows the effect of short time incubation with rhuEPO and further cultivation in the absence of rhuEPO on neuronal frataxin expression. P19 (neuronal-type) cells were incubated with rhuEPO for 1 hour. After washings, the cells were further incubated in the absence of rhuEPO for 48 hours. Cell lysates (50 µg protein) were separated on 12%

Figure 4A:
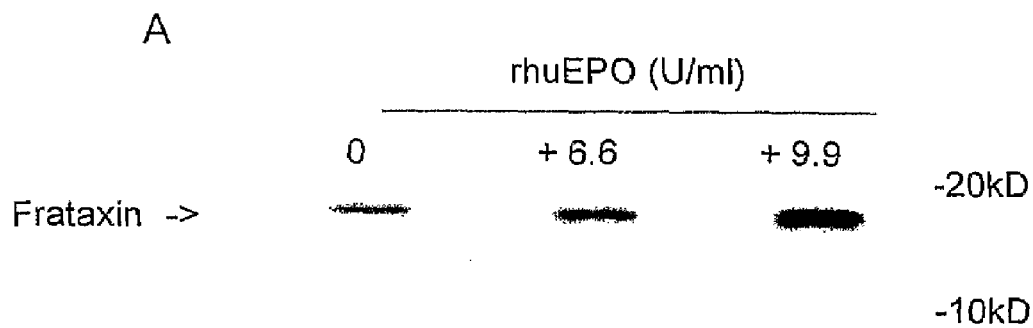
FIG. 4A is an image of a gel showing frataxin expression after administration of rhuEPO.
Figure 4B:
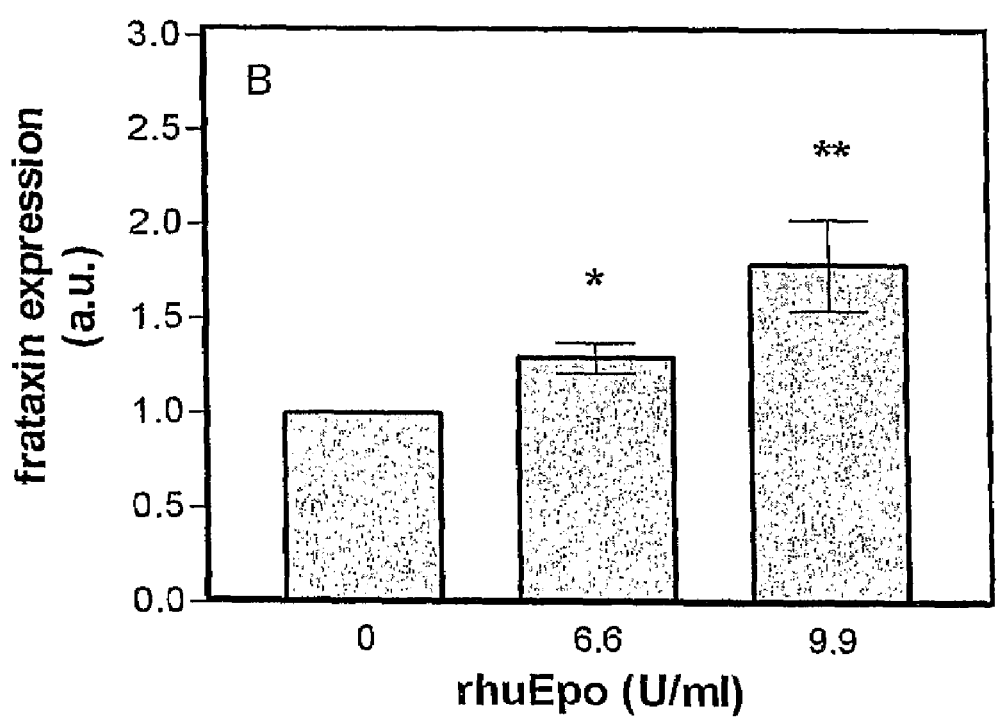
FIG. 4B is a graph showing frataxin expression as a function of rhuEPO.

SDS-polyacrylamide gel electrophoresis under non-reducing conditions and electroblotted onto nitrocellulose membranes. Western blot analysis was performed with a polyclonal antibody against human frataxin. FIGS. 4A and 4B show Western blot and Western blot densitometric analysis of frataxin expression respectively from three independent experiments. Density of the frataxin band of the control (untreated lymphocytes in the absence of rhuEPO from the same patient) was set as 1 a.u. (arbitrary units). Values represent means±SEM of 3 different experiments. Differences were examined for statistical significance using the paired t-test. Significant differences vs. control are marked in the figures with * ($p<0.05$) and ** ($p<0.01$).

From FIG. 4 it can be seen that short time incubation (for 1 hour) of P19 neuronal cells with rhuEPO and further cultivation in the absence of rhuEPO was sufficient to observe the same increase in frataxin-expression after 48 hours as in cells incubated for the whole incubation time with rhuEPO. These findings indicate that derivatives of erythropoietin with short plasma half-life such as asialoerythropoietin could also be effective to increase frataxin-expression in mammals.

What is claimed is:

1. A method of increasing frataxin expression in a subject having Friedreich's ataxia or a disease associated therewith, said subject being diagnosed as having decreased expression of frataxin, the method comprising:
providing a pharmaceutical composition having a therapeutically effective amount of erythropoietin or a derivative thereof having the biological activity of human erythropoietin sufficient for increasing expression of frataxin, said human erythropoietin or said derivative thereof is selected from the group of recombinant human erythropoietin, erythropoietin α, erythropoietin β, aranesp, asialoerythropoietin and carbamylated erythropoietin; and
administering the pharmaceutical composition to the subject having Friedreich's ataxia or the disease associated therewith being a neurodegenerative disease, said administering increases frataxin expression in the subject.

2. A method according to claim 1, wherein the subject has Friedreich's ataxia diagnosed by means of gene analysis and/or ELISA and/or real-time PCR and that expression of frataxin is decreased due to GAA-repeat-expansion or mutations on one or on both alleles in the frataxin gene.

3. A method according to claim 1, wherein said disease associated with Friedreich's ataxia is a neurodegenerative disease, the subject having decreased expression of frataxin.

4. A method according to claim 1, wherein the subject is diagnosed by means of gene analysis and/or ELISA and/or real-time PCR and that expression of frataxin is decreased due to GAA-repeat-expansion or mutations on one or on both alleles in the frataxin gene.

5. A method of increasing expression of frataxin in a subject, said subject being diagnosed as having decreased expression of frataxin, the method comprising:
providing a pharmaceutical composition having a therapeutically effective amount of an erythropoietin having the biological activity of human erythropoietin sufficient for increasing expression of frataxin, said erythropoietin is selected from the group of recombinant human erythropoietin, erythropoietin α, erythropoietin β, aranesp, asialoerythropoietin and carbamylated erythropoietin; and
administering the pharmaceutical composition to the subject so as to increase expression of frataxin in the subject.

6. A method as in claim 5, wherein the subject is diagnosed by means of gene analysis and/or ELISA and/or real-time PCR.

7. A method as in claim 5, wherein the expression of frataxin is decreased due to GAA-repeat-expansion or mutations on one or on both alleles in the frataxin gene.

8. A method as in claim 5, wherein the subject is diagnosed to have Friedreich's ataxia or a neurodegenerative disease associated with Friedreich's ataxia.

* * * * *